(12) United States Patent
Glynn et al.

(10) Patent No.: US 7,305,344 B2
(45) Date of Patent: Dec. 4, 2007

(54) WIRELESSLY LOADED SPEAKING CONSUMER PRODUCT CONTAINER METHOD AND SYSTEM

(75) Inventors: Kenneth P. Glynn, Flemington, NJ (US); Jerome R. Mahoney, Colts Neck, NJ (US)

(73) Assignee: iVoice, Inc., Matawan, NJ (US)

( * ) Notice: Subject to any disclaimer, the term of this patent is extended or adjusted under 35 U.S.C. 154(b) by 745 days.

(21) Appl. No.: 10/893,720

(22) Filed: Jul. 16, 2004

(65) Prior Publication Data

US 2005/0199526 A1 Sep. 15, 2005

Related U.S. Application Data (63) Continuation-in-part of application No. 10/801,391, filed on Mar. 15, 2004, now abandoned, which is a continuation-in-part of application No. 10/768,930, filed on Jan. 30, 2004.

(51) Int. Cl.
*G10L 21/00* (2006.01)

(52) U.S. Cl. .................. 704/270; 704/201; 704/260; 379/88.13; 379/88.17; 379/88.01; 206/534; 455/558

(58) Field of Classification Search .............. 704/270, 704/201, 260; 379/88.13, 88.17, 88.01; 206/534; 455/558
See application file for complete search history.

(56) References Cited

U.S. PATENT DOCUMENTS

| | | | |
|---|---|---|---|
| 5,014,798 A | 5/1991 | Glynn | |
| 5,633,916 A * | 5/1997 | Goldhagen et al. | 379/88.17 |
| 5,724,021 A * | 3/1998 | Perrone | 340/309.7 |
| 5,737,395 A * | 4/1998 | Irribarren | 379/88.13 |
| 5,774,865 A | 6/1998 | Glynn | |
| 5,794,039 A * | 8/1998 | Guck | 707/103 R |
| 5,835,455 A * | 11/1998 | Hanson et al. | 368/10 |
| 5,846,089 A | 12/1998 | Weiss et al. | |
| 5,881,890 A * | 3/1999 | Wiley | 209/703 |
| 5,917,429 A | 6/1999 | Otis, Jr. et al. | |
| 5,924,069 A * | 7/1999 | Kowalkowski et al. | 704/275 |
| 5,982,904 A * | 11/1999 | Eghtesadi et al. | 381/74 |
| 5,995,904 A * | 11/1999 | Willen et al. | 702/14 |
| 6,018,289 A * | 1/2000 | Sekura et al. | 340/309.4 |
| 6,021,433 A | 2/2000 | Payne et al. | |
| 6,031,895 A * | 2/2000 | Cohn et al. | 379/88.13 |
| 6,032,155 A | 2/2000 | de la Huerga | |
| 6,047,257 A * | 4/2000 | Dewaele | 704/270 |
| 6,092,726 A * | 7/2000 | Toussant et al. | 235/383 |

(Continued)

*Primary Examiner*—Vijay Chawan
(74) *Attorney, Agent, or Firm*—Kenneth P. Glynn (57) ABSTRACT

A method of communicating product use instructions to patient includes: (a.) providing a group of product container with microprocessors, and, (b.) providing a central processor separate from the product containers. Each product container has the microprocessor attached to the container. The microprocessor includes: (a)(i) a wave file receiving chip; (a)(ii) a wave file storage means; (a)(iii) a wave file audio playback means; (a)(iv) an audio playback start means; and (a)(v) a power supply within the microprocessor. The central processor includes: (b)(i) user input means; (b)(ii) text-to-speech means; (b)(iii) wave file means to create a wave file from the text-to-speech means; and (b)(iv) wireless transmission means to transmit the wave file to the microprocessor wave file receiving chips of a plurality of OTC containers simultaneously. Wireless transmission may be radio frequency (RF) transmission systems, infrared (IR) transmission systems and any other wireless transmission systems that are now available or may become available.

26 Claims, 4 Drawing Sheets

U.S. PATENT DOCUMENTS

| | | | |
|---|---|---|---|
| 6,101,338 A * | 8/2000 | Bernardi et al. ............. 396/287 |
| 6,133,904 A * | 10/2000 | Tzirkel-Hancock ......... 345/589 |
| 6,150,942 A | 11/2000 | O'Brien |
| 6,157,705 A * | 12/2000 | Perrone .................... 379/88.01 |
| 6,216,015 B1 * | 4/2001 | Hymel ....................... 455/558 |
| 6,294,999 B1 | 9/2001 | Yarin et al. |
| 6,380,858 B1 | 4/2002 | Yarin et al. |
| 6,394,278 B1 * | 5/2002 | Reed .......................... 209/44.4 |
| 6,463,462 B1 | 10/2002 | Smith et al. |
| 6,563,911 B2 | 5/2003 | Mahoney |
| 2005/0199525 A1 * | 9/2005 | Mahoney .................... 206/534 |

* cited by examiner

WIRELESSLY LOADED SPEAKING CONSUMER PRODUCT CONTAINER METHOD AND SYSTEM

REFERENCE TO RELATED CASES

This patent application is a continuation-in-part of U.S. copending application Ser. No. 10/801,391 filed on Mar. 15, 2004, now abandoned by an inventor herein, with common assignment of ownership, and entitled "Wirelessly Loaded OTC Speaking Medicine Container", which is a continuation-in-part of copending patent application Ser. No. 10/768,930 filed on Jan. 30, 2004, entitled "Wirelessly Loaded Speaking Medicine Container", by an inventor herein, with common assignment of ownership.

BACKGROUND OF THE INVENTION

1. Field of the Invention

The present invention relates to speaking consumer product containers, and, more particularly, first creating user instructions in a central computer, wirelessly transmitting those instructions to a plurality of substantially identical product containers, and storing them for subsequent audio playback by users. Thus, the present invention relates to both the method of performing these steps, and the combination of devices and software (the system) for doing this.

2. Information Disclosure Statement

The following prior art is representative of the state of the art in the field of pertinent medicine containers or the art pertaining to wireless communications:

U.S. Pat. No. 6,563,911 B2 describes the present invention a speech enabled automatic telephone dialer device, system, and method using a spoken name corresponding to name-telephone number data of computer-based address book programs. The invention includes user telephones connected to a PBX-type telephony mechanism, which is connected to a telephony board of a name dialer device. User computer workstations containing loaded address book programs with name-telephone number data are connected to the name dialer device. The name dialer device includes a host computer in a network; a telephony board for controlling the PBX for dialing; a memory within the host computer for storing software and name-telephone number data; and, software to access computer-based address book programs, to receive voice inputs from the PBX-type telephony mechanism, to create converted phonemes from names to match voice inputs with specific name-telephone number data from the computer-based address book programs for initiating an automatic dialing.

U.S. Pat. No. 6,463,462 B1 describes an automated system for delivery of messages to multiple recipients, and for processing of responses to the messages, includes a message client, message server, and system database. A message is created using universal message form. The message content can be translated in to multiple formats and sent to one or more different recipients using one or more different types of messaging devices, including pagers, telephones, fax machines, and e-mail readers. A recipient profile manager allows each recipient to select the messaging devices to be used for message delivery as well as preferred messaging schedules, priorities, and messages security. Receipt of the messages by the recipients is verified, response requirements collected and consolidated from multiple sources and presented to the message originator in structured format.

U.S. Pat. No. 6,394,278 B1 describes a system and method for assisting an operator in sorting mail includes a wireless headset equipped with a microphone, and a workstation that includes a processing unit, voice-recognition and voice-synthesis circuitry, and a database. In operation, addressee information spoken into the microphone is transmitted to the work station where it is used to search the database. Destination information from a matching database record is then output to the operator on one or more of a display terminal, head set speakers, and heads-up display fixed to the head-set. The convenience and enhanced capability provided by this system steaminess operator productivity and sorting volume. The embodiments disclosed herein are primarily directed to a headset that is operated completely remotely from the processing unit, and also to a head set comprising a heads up display having means by which an operator can access the database.

U.S. Pat. No. 6,380,858 B1 describes systems and methods that are provided for facilitating effective self-management of medication treatment by patients. A Smart Tray monitors and reports to third parties a patient's compliance with various medication treatment regimens. Medication containers are provided with electromagnetic tags that provide various informations about medicament contained within a respective container. A Smart Tray is equipped with a processor and reader that interrogates each respective electromagnetic tag to identify medicament(s) contained within each container. Using the retrieved information, a Smart Tray provided visual and/or audio signals to a patient to remind the patient when and how much of various medicaments to take. A Smart Tray also monitors, via the reader, when a mediation container is removed. A Smart Tray can communicate with one or more third parties, such as healthcare products and services via a computer network. In addition, a Smart Tray can communicate with various appliances and can modify medication regimens for particular medicaments in response to data received from various appliances.

U.S. Pat. No. 6,294,999 B1 describes systems and methods that are provided for facilitating effective self-management of medication treatment by patients. A Smart Tray monitors and reports to third parties a patient's compliance with various medication treatment regimens. Medication containers are provided with electromagnetic tags that provide various information about medicament contained within respective container. A Smart Tray is equipped with a processor and reader that interrogates each respective electromagnetic tag to identify medicament(s) contained within each container. Using the retrieved information, a Smart Tray provides visual and/or audio signals to a patient to remind the patient when and how many of various medicaments to take. A Smart Tray also monitors, via the reader, when a medication container is removed. A Smart Tray can communicate with one of more third parties, such as healthcare providers, pharmacies, and other suppliers of healthcare products and services via a computer network. In addition, a Smart Tray can communicate with various appliances and can modify medication regimens for particular medicaments in response to data received from various appliances.

U.S. Pat. No. 6,150,942 describes an interactive prescription compliance, and life safety system that provides remote and on site verification of procedures related to the health status of a person, including taking of medicines, responsiveness to queries, and attendance of health care and service providers in the home by providing for signals to and from a person's location, with alarm activation when a deviation from a preprogrammed procedure occurs.

U.S. Pat. No. 6,032,155 describes an invention that relates to a method and apparatus for administering prescribed medication to a patient. The prescribed medication administration system and apparatus dispense prescribed medication, verify the medication is given to a correct patient by and authorized healthcare worker and tracks and records the administration of the medication. The system utilizes a workstation connected to a database containing prescribed medication dose information for various patients. A healthcare worker uses the workstation to manually or automatically dispenses the medication the portable container. An information device is secured to the portable container during transport and administration of the medication to the intended patient. The information device prevents access to the medication or warns the healthcare worker of a potential error if the medication is delivered to the wrong patient or administered by an unauthorized healthcare worker. The information device records actual consumption information, and delivers this information back the workstation database or to a hospital or pharmacy database.

U.S. Pat. No. 6,021,433 describes a system and method for data communication connection on-line networks with on-line computers. The present system provides for broadcast of up to the minute notification centric data there by providing an instant call to action for users who are provided with the ability to instantaneously retrieve further detailed information. Information sources transmit data to a central broadcast server, which preprocesses the data for wireless broadcast. The notification centric portions of data are wirelessly broadcast to wireless receiving devices that are attached to computing devices. Upon receipt of the dada the computing device, the user is notified through different multimedia alerts that there is an incoming message. Wirelessly broadcasted URL's, associated with the data, are embedded in data packets and provide an automated wired or wireless connection back to the information source for obtaining detailed data.

U.S. Pat. No. 6,018,289 describes a prescription compliance device which aids patients in complying with instructions given by a physician for taking prescription medication. The device reminds a patient when the next dose of medication is to be taken and indicates whether a specified dose has been taken. The device includes a microcontroller, a display, a program memory for storing pre-programmed medication-taking regimens and for programming the device as to the time and day on which the first dose of medication is to be taken, a display which alternately displays the current time and a time at which a next dose of medication is to be taken, and an alarm which alerts the patient at times when a dose of medication is to be taken. The selector includes an event switch, which is activated by the patient after taking a dose of medication so as to record the taking of the medication and to cause the microcontroller to effect the display of the next time at which a dose of medication is to be taken. A memory may also be included to record the times at which a patient takes doses of medication. The device is small enough to be attached to medication containers, and includes a remote programming feature via a wireless link.

U.S. Pat. No. 5,917,429 describes a means which digital data are communicated between a portable data-gathering unit and a date-receiving unit without direct electrical connection by transmitting the data over a contactless connection system. In a preferred embodiment, data flow is bidirectional.

U.S. Pat. No. 5,846,089 describes a medicine container that provides audible dosage instructions in a voice recognizable to the user, so that the user, even with a sight or like disability, can rely on voice recognition as providing verification of the accuracy and particular appropriateness of the dosage instructions to the user of the medicine container.

U.S. Pat. No. 5,835,455 describes a reprogrammable device for removably receiving a medicine container and for providing audio instructions to a patient for taking a medication. When a medicine container is removed from the device by the patient so that the patient may take the medicine, the device can be activated to play a pre-recorded individualized message from the pharmacist providing the patient audio instructions for taking the medication.

U.S. Pat. No. 5,774,865 describes the patient compliance and monitoring device that utilizes a tray with a base for holding medicine containers such as bottles. Inside the base attached to the tray in a weight scale connected to a computer. Also connected to the computer are an alphanumeric keyboard and an LCD monitor which attached to the base. The computer entails a microprocessor connected to ROM and RAM and encoded with instruction sets to determine the dosage taken by a user as well as the date and time taken. The medicine containers are detected, preferably, by a bar code reader inside the base scanning bar code labels attached to the bottom of the medicine containers.

U.S. Pat. No. 5,014,798 describes a present invention that is directed to a cap for a medicine bottle for monitoring a patient's medicine compliance. In involves weighing a container of medicine with cap with includes scale means located therein which is connected to a computer chip with a display unit also located in or on the cap. The chip may store the starting weight or tare weight, plus total weight and when the container or medicine is picked up by the cap at any time, actual weight is fed to the chip. The computer chip may they determine the difference between the starting weight and/or display actual amount of medicine remaining or consumed. The container of medicine is reweighed from time to time with the cap and then chip may compare actual weight with compliance required weight to determine compliance and the cap may visually display the compliance results on the display unit to inform the patient. An optional audio assist may direct the patient to "call the doctor" if a significant compliance deviation is recognized.

Notwithstanding the prior art, the present invention is neither taught nor rendered obvious thereby.

SUMMARY OF THE INVENTION

The present invention relates to a method of communicating product use instructions to consumers. These instructions may include assembly instructions, utilization instructions, maintenance instructions or any combination of these or other instructions that a manufacturer or product seller may desire to communicate to the user (referred to herein as "product use" instructions), and may also include product warnings or the like. The present invention method includes: (a.) providing a plurality of product containers with microprocessors, and (b.) providing a central processor separate from the product containers and their microprocessors. Each product container includes a storage area for product and some type of closure, e.g., a cover, and has the microprocessor attached to the product container. The microprocessor includes: (a)(i) a wave file receiving chip; (a)(ii) a wave file storage means; (a)(iii) a wave file audio playback means; (a)(iv) an audio playback start means; and (a)(v) a power supply within the microprocessor, and adapted to power components of the microprocessor.

The central processor includes: (b)(i) user input means; (b)(ii) text-to-speech means; (b)(iii) wave file means to create a wave file from the text-to-speech means; and (b)(iv) wireless transmission means to wirelessly transmit the wave file from the central processor to the microprocessor wave file receiving chip. The phrase "wireless transmission means" shall include radio frequency (RF) transmission systems, infrared (IR) transmission systems and any other wireless transmission systems that are now available or may become available for a transmission of data over airwaves.

The method further includes: (c.) inputting the user input means to create product use instruction text; (d.) converting the text to electronic speech; (e.) creating a wave file with the electronic speech; (f.) transmitting the wave file to a plurality of microprocessor wave file receiving chips; and (g.) storing the received wave file for subsequent playback by users by activating the audio playback starting means. The plurality of product containers are provided with product of the same type and model the count of units of product being the same or different. The concept of the "product of the same type" may mean identical products or may mean different products that are similar enough that the same instructions would apply to all such products. For example, instructions for assembly of a bed frame would be identical for single bed frames, double bed frames and queen bed frames. Thus, since the only difference would be the length of the cross members, these products would be considered the same product for purposes of this invention because the same assembly instructions would apply. Likewise, a plurality of different paintings in frames would have different renditions and perhaps even different size frames, but the same instructions would apply to all of these for hanging the frames. Also, the same wave file could be used for a package or container having two molly screws or for one having twenty five molly screws; likewise, for a four ounce container of wrinkle-removing facial cream and a twenty ounce container of the same product.

In the present invention method, the product itself may be added to the container before and/or during and/or after the transmittal of the wave file to the receiving chip of the container.

In some preferred embodiments, the present invention method central processor is a computer system and the user input means is a conventional computer user input means selected from keyboard, mouse, ball and touch pad.

In other preferred embodiments of the present invention method, the following steps are included: (h.) creating a unique identifier in the central processor; (i.) transmitting the unique identifier to the microprocessor; and (j.) providing accessing means for accessing the unique identifier from the microprocessor. This optional feature will provide key information to a user or other person accessing the information, such as the specific lot number of a food or the specific model and id number of a television, computer, stereo or the like.

The microprocessor may be attached to a bottom of the product container, to a top of the product container, to a wall of the product container or to a cap, cover or other closure.

In some embodiments, the user input means is a microphone and the central processor includes conversion means for converting speech to electronic input.

An alternative embodiment present invention method of communicating product use instructions to a user includes: (a.) providing a plurality of product containers, each product container including a storage area for product, and a microprocessor attached to the product container. The microprocessor includes: (a)(i) a wave file receiving chip; (a)(ii) a wave file storage means; (a)(iii) a wave file audio playback means; (a)(iv) an audio playback start means; and (a)(v) a power supply within the microprocessor, and adapted to power components of the microprocessor; and (b.) providing a central processor separate from the plurality of product containers. The central processor includes: (b)(i) user input means for inputting electronic product use instruction input; (b)(ii) wave file means to create a wave file from the electronic product use instruction input from the input means; and (b)(iii) wireless transmission means to wirelessly transmit the wave file from the central processor to the microprocessor wave file receiving chip. This alternative method also includes the steps of: (c.) inputting product use instructions with the user input means to create electronic input; (d.) creating a wave file with the electronic input; (e.) transmitting the wave file to the microprocessor wave file receiving chips; (f.) storing the transmitted wave file for subsequent audio playback by users by activating the audio playback starting means.

The present invention also relates to a system (combination of equipment and software) for communicating product use instructions to a user by wireless communication from a central processor to a plurality of product containers for subsequent audio speech playback from the product containers to users. The system includes: (a.) a plurality of product containers, each product container including a storage area for product, and a microprocessor attached to the product container, the microprocessor including: (a)(i) a wave file receiving chip; (a)(ii) a wave file storage means; (a)(iii) a wave file audio playback means; (a)(iv) an audio playback start means; and (a)(v) a power supply within the microprocessor, and adapted to power components of the microprocessor; and (b.) a central processor separate from the plurality of product containers, the central processor including: (b)(I) user input means; (b)(ii) text-to-speech means; (b)(iii) wave file means to create a wave file from the text-to-speech means; and (b)(iv) wireless transmission means to wirelessly transmit the wave file from the central processor to the microprocessor wave file receiving chips of the plurality of product containers.

An alternative embodiment present invention system for communicating product use instructions to a user by wireless communication from a central processor to a plurality of product containers for subsequence audio speech playback from the product containers to users, includes: (a.) a plurality of product containers including a storage area for product, and a microprocessor attached to each product container, the microprocessor including: (a)(i) a wave file receiving chip; (a)(ii) a wave file storage means; (a)(iii) a wave file audio playback means; (a)(iv) an audio playback start means; and (a)(v) a power supply within the microprocessor, and adapted to power components of the microprocessor. It also includes (b.) a central processor separate from the product. The central processor includes: (b)(i) user input means said electronic product instrument input. (b)(ii) wave file means to create a wave file from the text-to-speech means; and (b)(iii) wireless transmission means to transmit the wave file from the central processor to the microprocessor wave file receiving chip.

These systems may be computer systems, and the user input means may be a conventional computer user input means selected from keyboard, mouse, ball and touch pad.

The systems may optionally include: (h.) means for creating a central processor unique identifier in the central processor; (i.) means for transmitting said unique identifier to the microprocessor; and (j.) providing accessing means for accessing the central processor unique identifier from the microprocessor.

The systems may be system wherein the user input means is a microphone and the central processor included reversion means for converting speech to electronic input.

All of the present invention methods and systems may include additional features. For example, the wave file may include both user instructions and product warnings. Alternatively, there may be two microprocessor capabilities for handling two or more separate wave files and two or more start means and the user may push one button for instructions and another for product warning information (insert warnings). In yet other embodiments, with or without the foregoing additional features, the cap or other closure may be wired so that when it is first opened, an automatic start occurs for a first playing of the instructions or warnings or both. In other words, this would be a system wherein the user would do nothing except open a container and an automatic message would audibly play out to the user. Preferably, the microprocessor could be programmed to recognize the start signal from cap removal only once, for first use playing, or, alternatively, repeatedly.

BRIEF DESCRIPTION OF THE DRAWINGS

The present invention should be more fully understood when the specification herein is taken in conjunction with the drawings appended hereto wherein.

DETAILED DESCRIPTION OF THE PRESENT INVENTION

Figure 1:
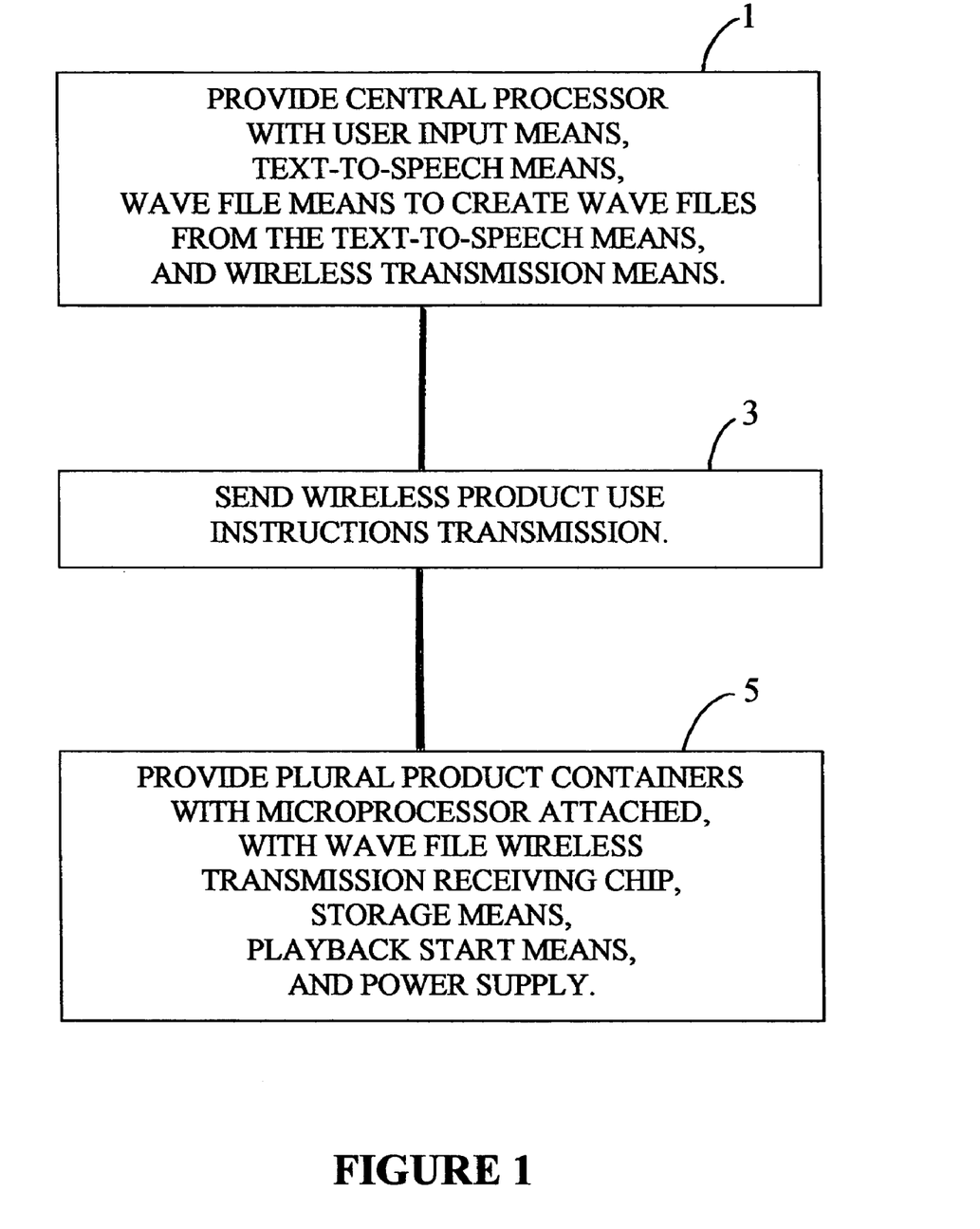
FIG. 1 illustrates a schematic diagram of one preferred embodiment of the present invention method and system.

FIG. 1 illustrates a schematic diagram of one preferred embodiment of the present invention method and system. In FIG. 1, central processor 1 may be any type of central processor that is available and is capable of supporting the necessary hardware and software to perform the functions described herein. Thus, the central processor 1 could be a collection of internet or intranet connected units, a server, a stand alone computer, a PC, a notebook, a lap top or even a multimedia system or handheld computer, or a device that includes a computer.

Central processor 1 requires user input means and this could be any available user means, but is typically a ball, a mouse, a key pad, a microphone, or combinations of these. It also includes text-to-speech means and these are well known systems that convert electronic text to speech. These are well known programs and would be familiar to one of ordinary skill in this art. For example, U.S. Pat. No. 6,394,278 B1 and patents cited therein show speech-to-text and text-to-speech capabilities.

Central processor 1 also includes wave file means to create wave files from the text-to-speech means, as well as wireless transmission means. Wave files creation and wireless transmission, not in the present invention system, are known to the artisan and are described in the cited prior above.

The user will use the input means to create the wave files by normal input of product use instructions, and these are wirelessly transmitted 3 to a plurality of product containers 5. These may be done in batches, sequentially, simultaneously, or in group/step functions. Typically, these are hundreds or thousands or millions of containers with the same product that would utilize the same product instructions.

Each product container 5 includes a microprocessor attached to it that receives the wave file wireless transmission, storage means for storing the wave file and whatever additional software that may be required to create audible speech patterns. Each of the plurality of product containers 5 also include playback and playback start means as well as a power supply. Typically, the microprocessors would be located on the bottom of the product containers and would be cylindrical or otherwise conformed to the general shape of the product container. Alternatively, it could have any convenient shape and be located on any area of the product container or its cover. It would include a start mechanism that could be a button or switch, or its equivalent. A user would simply activate the start mechanism and the microprocessor would automatically playback the product use instructions.

Figure 2:
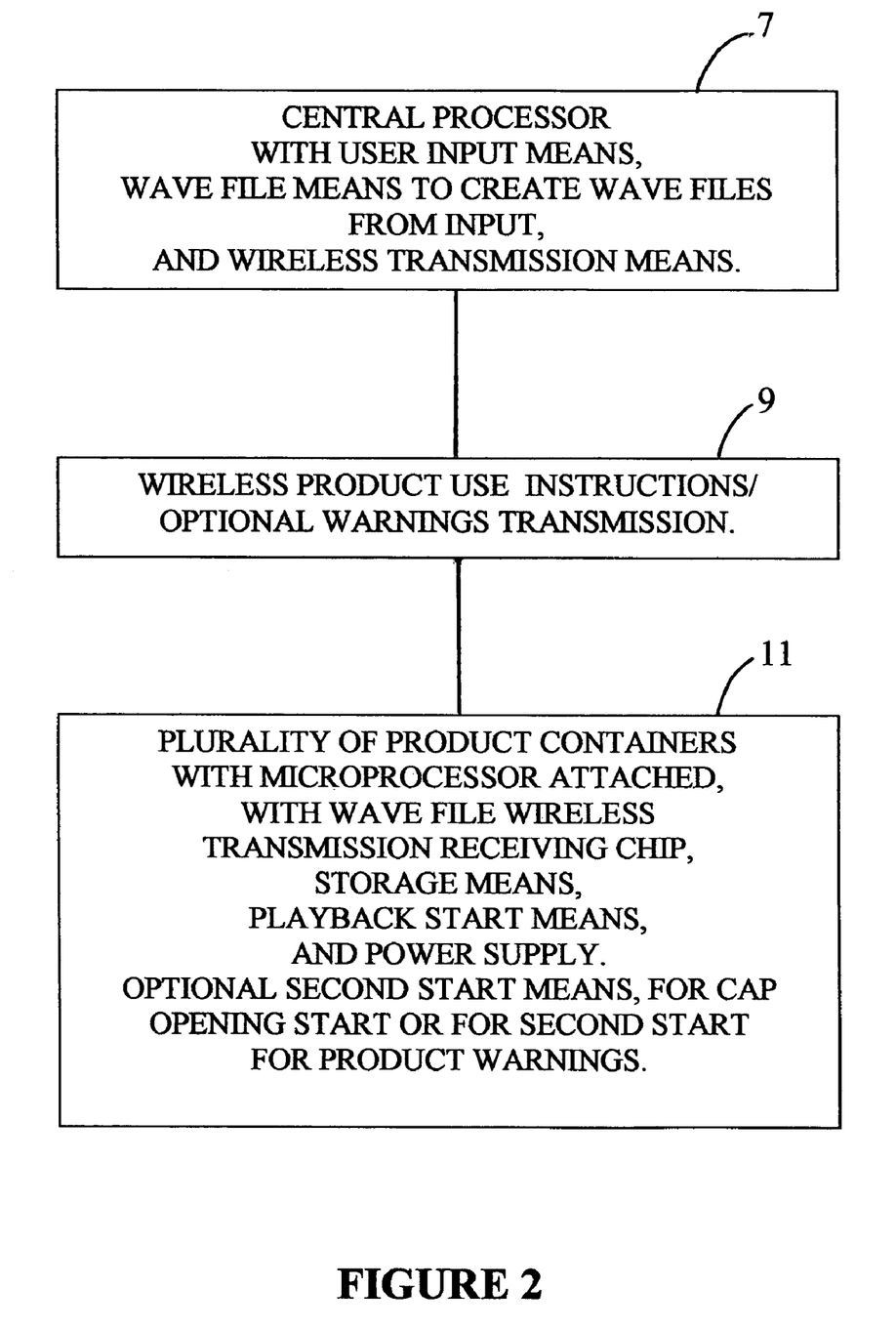
FIG. 2 shows another schematic diagram of an alternative embodiment of a present invention method and system.

FIG. 2 shows another schematic diagram of an alternative embodiment of a present invention method and system. In this embodiment, the central processor 7 functions similarity to central processor 1 above but creates wave files directly from inputs and transmits 9 these to a plurality of product containers 11. Product containers 11 function similarity to product containers 5 of FIG. 1, except that an optional second start means is included on the product containers with, for example, dual microprocessor capabilities. This could be a cover-connected second start mechanism that would automatically play the first time the cover is removed, or it could be a second start mechanism for playing product warnings.

Figure 3:
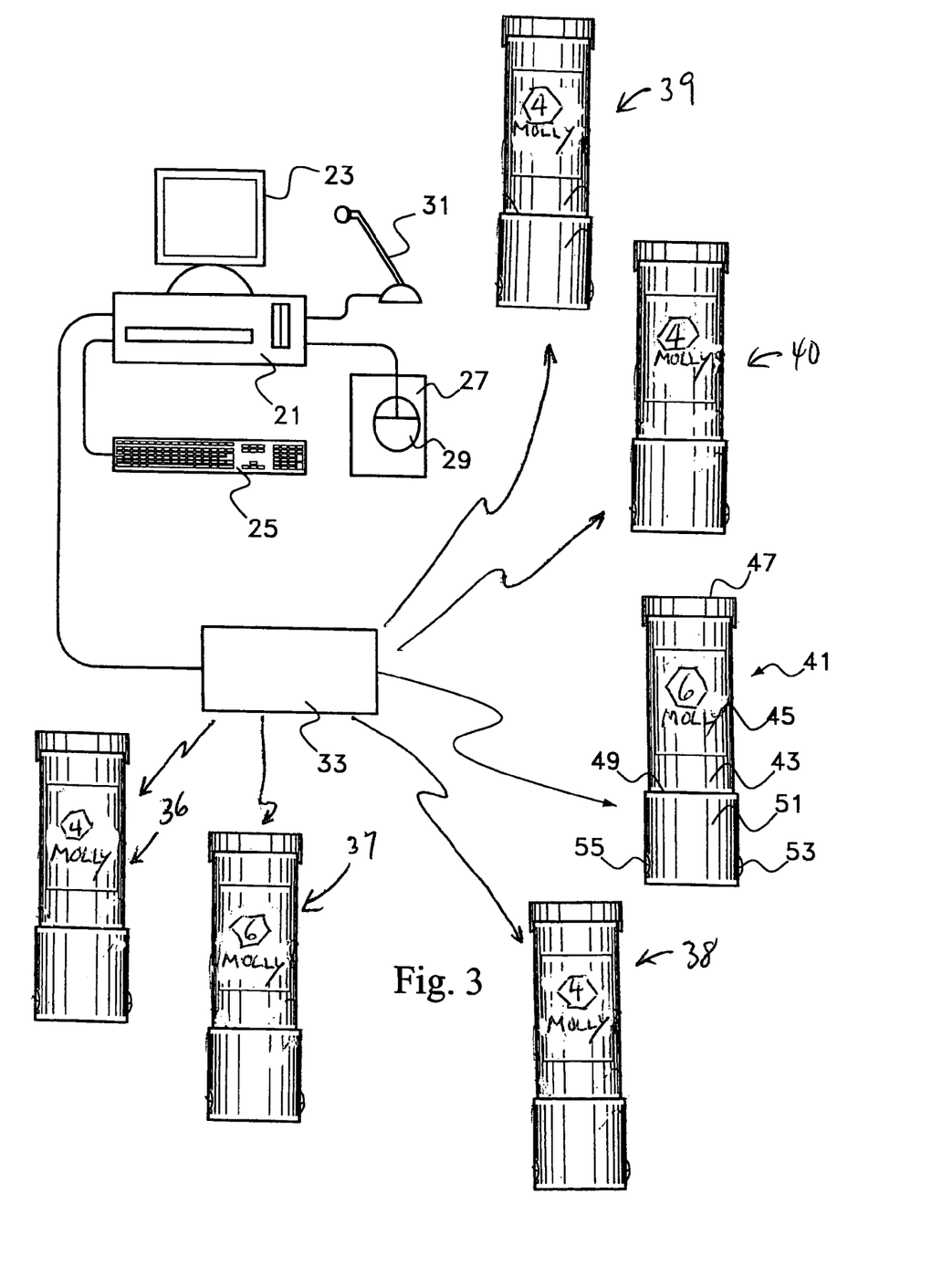
FIG. 3 shows a diagrammatic representation of a present invention system.

FIG. 3 shows a diagrammatic representation of a present invention system. There is a central processor, in this case, computer 21 with monitor 23, as well as impute means which, in this embodiment, are shown to be keyboard 25, mouse 27 and pad 29 and microphone 31. A slider, joystick, or touch ball or any other input means could be included in addition to or in place of those shown in the figure.

Computer 21 could be a master server, a personal computer, or any other type of computer. Computer 21 is connected to transmitter 33 for short distance transmission of the wave file. While this is shown as a separate device wired to computer 21, it could be built in to a computer unit with appropriate hardware, software and middleware. This wirelessly transmits the wave file package with optional unique identifier information to a plurality of product containers 36, 37, 38, 39, 40, and 41, and, more particularly to their microprocessors. Details are shown with respect to container 41, which includes microprocessor 51 attached to container bottom 49. Container 41 includes a typical product storage area 43, a label 45 and a cover 47. Playback start button 53 enables a user to playback the received and stored wave file packet product use instruction as often as desired.

Microprocessor 51 includes a wave file wireless transmission receiving chip and a power supply, as well as storage means and optional unique identifier retrieval means. This could be a plug in port such as port 55.

Figure 4:
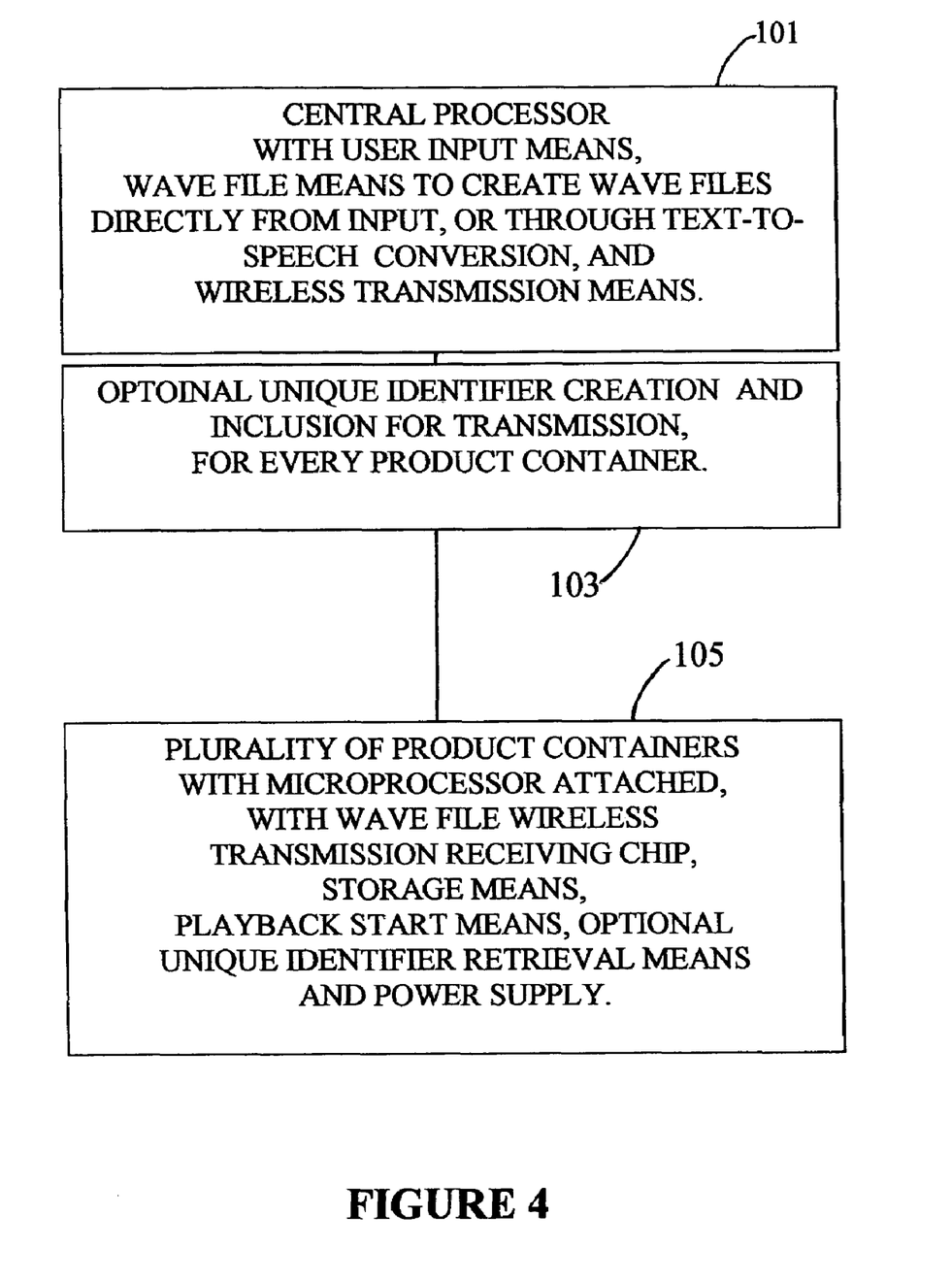
FIG. 4 illustrates another preferred embodiment of the present invention method and system for wirelessly transferring product use instructions from a central processor to a product container for subsequent audio playback by a user.

FIG. 4 illustrates another preferred embodiment of the present invention system for wirelessly transferring product use instructions from a central processor to a product container for subsequent audio playback by a user. Central processor 101 may be arranged as in FIG. 1 or as in FIG. 2 above, and, includes optional unique identifier capabilities 103. This includes sufficient equipment and software to create a unique identification code for each and every product container to which a wave file is sent. This code could be any combination of numbers and/or letters and/or symbols.

In one preferred embodiment of the present invention, the system is provided to a pharmaceutical manufacturer operator or similar functionary, may input the appropriate product use instruction for creation wave file, for subsequent transmission to the receiving product container microprocessors. A number of variations are possible. For example, the wave file may include a unique identifier along with other information, such as the manufacturers names, the contents of the container, product codes, bar code equivalents, etc.

In one preferred embodiment, the software is set up to create records for the manufacturer, such as batch numbers, processing dates, and even print out labels for the medicine containers and create a wave file, with requiring only a single set of inputs. The unique identifier may include any or all of the previously stated information for each batch of particular product containers.

In another embodiment, the software program of the central processor may contain list of various model products with different instructions so that an operator may click a specific product model, and a specific set of product use instructions will appear. The operator will click to confirm and this may be transmitted to the desired lots of product. A preexisting wave file corresponding to that selection by the operator will thus be automatically brought up and wirelessly transmitted to the product container microprocessors when desired and an operator sends an appropriate directive.

Obviously, numerous modifications and variations of the present invention are possible in light of the above teachings. It is therefore understood that within the scope of the appended claims, the invention may be practiced otherwise than as specifically described herein.

What is claimed is:

1. A method of communicating product use instructions to a plurality of consumers of the same products, which comprises:
   (a.) providing a plurality of product containers, each of said plurality of product containers including a storage area for a product, and a microprocessor attached to each of said plurality of product containers, said microprocessor including:
      (a)(i) a wave file receiving chip;
      (a)(ii) a wave file storage means;
      (a)(iii) a wave file audio playback means;
      (a)(iv) an audio playback start means; and
      (a)(v) a power supply within said microprocessor adapted to power components of said microprocessor;
   (b.) providing a central processor separate from said plurality of product containers, said central processor including:
      (b)(i) user input means;
      (b)(ii) text-to-speech means;
      (b)(iii) wave file means to create a wave file from said text-to-speech means; and
      (b)(iv) wireless transmission means to wirelessly transmit said wave file from said central processor to said microprocessor wave file receiving chip;
   (c.) inputting said user input means to create product use instruction text;
   (d.) converting said text to electronic speech;
   (e.) creating a wave file with said electronic speech;
   (f.) transmitting said wave file to said plurality of product container microprocessor wave file receiving chips;
   (g.) storing said wave file in said microprocessors for subsequent playback by users by activating said audio playback starting means; and,
   (h.) providing product to said storage area of each of said plurality of product containers, said product being substantially the same product for each of said plurality of product containers.

2. The method of claim 1 wherein said central processor is a computer system and said user input means is a conventional computer user input means selected from keyboard, mouse, ball and touch pad.

3. The method of claim 1 further comprising:
   (i.) creating a unique identifier for product identification, in said central processor;
   (j.) wirelessly transmitting said unique identifier to said microprocessor; and
   (k.) providing accessing means for accessing said unique identifier from said microprocessor.

4. The method of claim 1 wherein each said microprocessor is attached to at least one of a bottom, a top, a side of each said product container.

5. The method of claim 1 wherein said user-input means is a microphone and said central processor includes conversion means for converting speech to electronic input.

6. The method of claim 1 wherein said central processor further includes: (a)(vi) a preset data collection of product use instructions, including for at least two different types of products, and sufficient software to permit a user to select appropriate product use instructions corresponding to a specific product for a specific plurality of identical product containers having substantially the same product to be stored therein.

7. A method of communicating product use instructions to a plurality of consumers, which comprises:
   (a.) providing a plurality of product containers, each of said plurality of product containers including a storage area for product, and a microprocessor attached to each product container, said processor including:
      (a)(i) a wave file receiving chip;
      (a)(ii) a wave file storage means;
      (a)(iii) a wave file audio playback means;
      (a)(iv) an audio playback start means; and
      (a)(v) a power supply within said microprocessor adapted to power components of said microprocessor;
   (b.) providing a central processor separate from said plurality of product containers, and said central processor including:
      (b)(i) user input means for inputting electronic product use instruction input;
      (b)(ii) wave file means to create a wave file from said electronic product use instruction input from said input means; and
      (b)(iii) wireless transmission means to wirelessly transmit said wave file from said central processor to said microprocessor wave file receiving chip;
   (c.) inputting product use instructions with said user input means to create electronic input;

(d.) creating a wave file with said electronic input;
(e.) transmitting said wave file to said plurality of product container microprocessor wave file receiving chips;
(f.) storing said transmitted wave file wireless transmission for subsequent audio playback by users by activating said audio playback starting means; and
(g.) providing a product to said storage area of each of said plurality of product containers, said product being substantially the same product for each of said plurality of product containers.

8. The method of claim 7 wherein said central processor is a computer system and said user input means is a conventional computer user input means selected from the group consisting of keyboard, mouse, ball and touch pad.

9. The method of claim 7 further compromising:
(h.) creating a unique identifier for product identification, in said central processor;
(i.) wirelessly transmitting said unique identifier to said microprocessor; and
(j.) providing processing means for accessing said unique identifier from said microprocessor.

10. The method of claim 7 wherein each said microprocessor is attached to at least one of a bottom, a top, a side of each said product container.

11. The method of claim 7 wherein said user input means is a microphone and said central processor includes conversion means for converting speech to electronic input.

12. The method of claim 7 wherein said central processor further includes: (a)(vi) a preset data collection of product use instructions, including for at least two different product types, and sufficient software to permit a user to select appropriate product use instructions corresponding to a specific product for a specific plurality of product containers having the substantially the same product to be stored therein.

13. A system for communicating product use instructions to consumers by wireless communication from a central processor to a plurality of product containers for subsequent audio speech playback from said product containers to consumers, which comprises:
(a.) a plurality of product containers, said product containers including a storage area for product, and a microprocessor attached to each of said plurality of product containers, said microprocessor including:
(a)(i) a wave file receiving chip;
(a)(ii) a wave file storage means;
(a)(iii) a wave file audio playback means;
(a)(iv) an audio playback start means; and
(a)(v) a power supply within said microprocessor, and adapted to power components of said microprocessor;
(b.) a central processor separate from said plurality of product containers, said central processor including:
(b)(i) user input means;
(b)(ii) text-to-speech means;
(b)(iii) wave file means to create a wave file from said text-to-speech means; and
(b)(iv) wireless transmission means to wirelessly transmit said wave file from said central processor to said microprocessor wave file receiving chip;
(c.) a product in each said product storage area of said plurality of product containers.

14. The system of claim 13 wherein said central processor is a computer system and said user input means is a conventional computer user input means selected from keyboard, mouse, ball and touch pad.

15. The system of claim 13 further comprising:
(d.) means for creating a unique identifier for product identification, in said central processor, for each of said plurality of product containers;
(e.) means for wirelessly transmitting said unique identifier to each said microprocessor; and
(f.) accessing means for accessing each said unique identifier from each said microprocessor.

16. The system of claim 13 wherein each said microprocessor is attached to at least one of a bottom, a top, a side of each said product container.

17. The system of claim 13 wherein said user input means is a microphone and said central processor included conversion means for converting speech to electronic input.

18. The system of claim 13 wherein each said product container microprocessor includes a first microprocessor capability and a second microprocessor capability, and said first microprocessor capability is adapted to receive product use instructions and said second microprocessor capability is adapted to receive product warning information; and
further wherein there are two audio playback start means, a first for said first microprocessor capability, and a second for said second microprocessor capability.

19. The system of claim 13 wherein each said product container includes a container cover, and a container cover connection area, and said container cover connection area includes a cover-opening audio playback start means connected to said microprocessor, such that when a cover is opened for a first time, wave file audio playback is initiated.

20. A system for communicating product use instructions to a consumer by wireless communication from a central processor to a plurality of product containers for subsequence audio speech playback from said plurality of product containers to consumers, which comprises:
(a.) a plurality of product containers including a storage area for product, and a microprocessor attached to each said product container, said processor including:
(a)(i) a wave file receiving chip;
(a)(ii) a wave file storage means;
(a)(iii) a wave file audio playback means;
(a)(iv) an audio playback start means; and
(a)(v) a power supply within said microprocessor, and adapted to power components of said microprocessor;
(b.) a central processor separate from said plurality of product containers, and said central processor including:
(b)(i) user input means for inputting electronic product use instruction input;
(b)(ii) wave file means to create a wave file from said electronic product use instruction input from said input means; and
(b)(iii) wireless transmission means to wirelessly transmit said wave file from said central processor to said microprocessor wave file receiving chip:
(c.) a product in each said product storage area of said plurality of product containers.

21. The system of claim 20 wherein said central processor is a computer system and said user input means is a conventional computer user input means selected from keyboard, mouse, ball and touch pad.

22. The system of claim 20 wherein comprising:
(d.) means for creating a unique identifier for product identification, in said central processor for each of aid plurality of product containers;

(e.) means for wirelessly transmitting said unique identifier to each said microprocessor; and (f.) accessing means for accessing each said unique identifier from each said microprocessor.

23. The system of claim 20 wherein each said microprocessor is attached to at least one of a bottom, a top, a side of each said product container.

24. The system of claim 20 wherein said user input means is a microphone and said central processor includes conversion means for converting speech to electronic input.

25. The system of claim 20 wherein each of said plurality of product container microprocessors include a first microprocessor capability and a second microprocessor capability, and said first microprocessor capability is adapted to receive product use instructions and said second microprocessor capability is adapted to receive product warning information; and further wherein there are two audio playback start means, a first for said first microprocessor capability, and a second for said second microprocessor capability.

26. The system of claim 20 wherein each said product container includes a container cover, and a container cover connection area, and said container cover connection area includes a cover-opening audio playback start means connected to said microprocessor, such that when a cover is opened for a first time, wave file audio playback is initiated.

* * * * *